United States Patent [19]

Farrar et al.

[11] Patent Number: 4,980,434

[45] Date of Patent: Dec. 25, 1990

[54] ABSORBENT POLYMERS, THEIR MANUFACTURE AND USES

[75] Inventors: David Farrar; Peter Flesher; Malcolm Hawe, all of West Yorkshire, England

[73] Assignee: Allied Colloids Limited, England

[21] Appl. No.: 162,134

[22] Filed: Feb. 29, 1988

Related U.S. Application Data

[63] Continuation of Ser. No. 894,345, Aug. 7, 1986, abandoned, which is a continuation-in-part of Ser. No. 766,097, Aug. 15, 1985, Pat. No. 4,702,844.

[30] Foreign Application Priority Data

| Aug. 15, 1984 | [GB] | United Kingdom | 8420694 |
| Aug. 15, 1984 | [GB] | United Kingdom | 8420695 |
| Aug. 15, 1984 | [GB] | United Kingdom | 8420693 |
| Aug. 12, 1985 | [GB] | United Kingdom | 8520218 |
| Feb. 14, 1986 | [GB] | United Kingdom | 8603654 |

[51] Int. Cl.$^5$ .................. C08F 30/04; C08F 12/30; C08F 20/54; A61F 13/15
[52] U.S. Cl. .................. 526/240; 526/287; 526/303.1; 526/307; 526/307.2; 526/307.3; 526/307.5; 526/307.6; 526/310; 526/318.4; 526/318.41; 526/332; 526/320; 604/372
[58] Field of Search .................. 526/307, 310, 322.2, 526/240, 287, 303.1, 307, 307.2, 307.3, 307.5, 307.6, 310, 332, 320, 318.4, 318.41; 604/372

[56] References Cited

U.S. PATENT DOCUMENTS

| 3,436,378 | 4/1969 | Azorlosa et al. | 526/333 |
| 3,499,876 | 3/1970 | Field et al. | 526/332 |
| 3,880,818 | 4/1975 | Shen et al. | 526/322 |
| 4,224,427 | 9/1980 | Mueller et al. | 526/93 |
| 4,227,582 | 7/1981 | Mueller | 526/264 |
| 4,277,582 | 7/1981 | Mueller et al. | 526/332 |
| 4,535,098 | 8/1985 | Evani et al. | 521/149 |

FOREIGN PATENT DOCUMENTS 7104037 11/1971 Netherlands .

*Primary Examiner*—Peter F. Kulkosky
*Attorney, Agent, or Firm*—Andrus, Sceales, Starke & Sawall

[57] ABSTRACT

The properties of absorptive synthetic polymer particles formed by polymerisation of water soluble monomers such as sodium acrylate or acrylamide with a cross linking agent are improved, especially as regards absorptive capacity for aqueous electrolytes, by copolymerising the monomers with an ethylenically unsaturated monomer that includes a pendant group $-A_mB_nA_pR$ where B is ethyleneoxy, n is at least 2, A is propyleneoxy or butyleneoxy, m and p are each less than n and are preferably zero, and R is a hydrophobic group.

13 Claims, No Drawings

ABSORBENT POLYMERS, THEIR MANUFACTURE AND USES

This application is a continuation of copending application Ser. No. 06/894,345 filed Aug. 7, 1986, now abandoned, which in turn is a continuation-in-part application of copending application Ser. No. 766,097 filed Aug. 15, 1985 U.S. Pat. No. 4,702,844.

It is known that a continuous phase of an aqueous medium can be thickened by the presence of high molecular weight synthetic polymers either in solution or in the form of swollen, very small, particles (generally below 2 microns dry size). If the polymers are in solution the thickening is conventionally probably due to entanglement of polymeric chains. If the polymers are swollen and insoluble the thickening is probably due to interparticulate attraction and solvent immobilisation.

It is known that thickening of a continuous aqueous phase can be improved in some instances by including in the polymer pendant hydrophobic groups. In addition to the mechanisms of interparticulate attraction and solvent immobilisation an additional effect occurs within the continuous phase that gives the improved properties, and this additional effect is believed to be association within the aqueous phase between the hydrophobic groups in adjacent molecules. The polymers containing such groups are often referred to as associative thickeners.

Various ways of introducing the hydrophobic groups have been proposed. In EP No. 48094 the hydrophobic group is introduced as a polymerisation initiator or chain transfer agent in the polymerisation of acrylamide. In EP No. 63018 and U.S. Pat. Nos. 4,423,199 and 4,524,175 the hydrophobic group is introduced as a substituent in acrylamide. In JP No. 60-235815A the pendant hydrophobic group is introduced as a vinyl ether.

In U.S. Pat. No. 3,915,921 and U.S. Pat. No. 4,190,562 the hydrophobic group is introduced as a $C_{10-30}$ alkyl ester of (meth) acrylic acid. In U.S. Pat. Nos. 4,138,381, 4,268,641, 4,384,096 and 4,463,151, EP No. 13836 and EP No. 109820 and in GB No. 1,167,524 an ester is formed between an unsaturated acid and a hydrocarbyl ether of a polyalkylene glycol.

In GB No. 1,167,524 the hydrophobic groups are introduced as an allyl ether or an unsaturated carboxylic ester and in GB No. 1,273,552 the hydrophobic groups are introduced as an allyl ether. It is well known that allyl monomers, even when present in very small quantities, make it difficult to obtain high molecular weight (see for instance "Functional Monomers" Volume 1 edited by Yocum and Nyquist page 384) and in U.S. Pat. No. 4,451,628 allyl sulphonate is used to depress the molecular weight of copolymers. It is apparent that the techniques used in these British patents are techniques that favour the formation of low molecular weight. For instance in example 13 of GB No. 1167524 a copolymer of an acrylic ester carrying the hydrophobic group and acrylamide is made and the molecular weight is depressed by conducting the polymerisation in the presence of isopropanol. Accordingly the polymers of these two patents are inevitably of low molecular weight and this may explain why these polymers have not been commercially successful despite the success of the high molecular weight polymers such as those made by oil-in-water emulsion polymerisation, generally as indicated in EP No. 13836.

All these patents on associative thickeners are concerned with thickening a large volume of a continuous aqueous phase using a minor amount of polymer so as to produce a thickened fluid medium. The associative effect between the polymers involves association within the continuous phase between polymers that are in solution and/or interparticulate attraction between very small undissolved particles of the polymers.

In contrast to processes where a polymer thickens a continuous phase are processes in which large polymer particles absorb aqueous fluid without thickening a continuous aqueous phase, the total amount of aqueous phase generally being less than will provide a continuous aqueous phase.

Conventional water absorbent polymer particles for such purposes have a size greater than 20 microns and are made by polymerisation of water soluble ethylenically unsaturated monomer, often acrylic acid and/or acrylamide, in the present of cross-linking agent to prevent dissolution, minimise tackiness, and control absorptive capacity.

In U.S. Pat. Nos. 4,062,817 and 4,190,562 water absorbent polymers incorporate a $C_{10-30}$ alkyl (meth) acrylate and in most instances the polymer is soluble.

One problem with conventional absorbent polymers is that their absorbency for aqueous electrolyte is rather low. Another problem is that attempts at increasing absorbency by increasing the swellability of the polymer, for instance by reducing cross linking agent, tend to result in the formation of a polymer that is very sticky, and this is undesirable.

An absorbent polymer according to the invention comprises water insoluble, water-swellable particles at least 20 µm in size and is formed from (a) 30 to 99% water soluble ethylenically unsaturated monomer, (b) 0 to 40% water insoluble ethylenically unsaturated monomer, (c) 0.0001 to 1% copolymerisable polyethylenically unsaturated monomer or other cross linking agent and (d) 1 to 70% of ethylenically unsaturated monomer that carries a pendant group $-A_mB_nA_pR$ wherein B is ethyleneoxy, n is an integer of at least 2, A is propyleneoxy or butyleneoxy, m and p are each an integer less than n and preferably below 2 and most preferably zero, and R is a hydrophobic group containing at least 8 carbon atoms. Throughout this specification all percentages are by weight unless otherwise specified.

R can be a polyoxyalkylene chain where the alkylene groups wholly or mainly are propylene or higher but preferably is a hydrocarbyl group. The hydrocarbyl group generally contains from 8 to 30, preferably 10 to 24 and most preferably 12 to 18 carbon atoms. It may be selected from alkyl, for instance octyl, lauryl or stearyl, aralkyl such as 2-phenyl-ethyl ($-C_2H_4Ph$), aryl such as naphthyl, alkaryl such as alkyl phenyl wherein the alkyl group generally contains 6 to 12 carbon atoms, cycloalkyl (including polycyclic alkyl groups), or mixtures of one or more such groups. Preferred hydrocarbyl groups are alkyl and alkaryl groups. Any of these groups may additionally be substituted provided the substituents do not render the pendant group hydrophilic to an extent that the desired improvement in properties due to the hydrophobic group is lost.

The polyoxyethylene chain ($n \geq 2$) may be interrupted by oxypropylene groups but preferably m and p are each zero. The properties of the final polymer can be controlled by appropriate selection of n, m, p and R.

The amount of monomer (d) is generally from 3 to 50% by weight, often 3 to 30%.

We have found that the polymers surprisingly have very good absorptive capacity for electrolytes and that it is possible to obtain an excellent combination of absorptive capacity and non-tackiness for aqueous media in general, and especially for aqueous electrolytes.

The improvement in absorptive capacity for electrolytes increases with increasing length of the polyethyleneoxy chain and so best results are obtained when the group R is separated from the ethylenic carbon atom by a long chain. Preferably n is at least 5 and most preferably at least 10 with best results generally being obtained when it is 10 or more, e.g., up to 20 or 50 or even 100.

The ethylenically unsaturated monomer (d) carrying the group $-A_mB_nA_pR$ is preferably a monomer of the formula $$R^1CH=C(R^2)\ QA_mB_nA_pR$$

where
A, B, n, m, p and R are as defined above and
$R^1 = COOR^3$ or $QA_mB_nA_pR$ when $R^2=H$ and $Q\neq CH_2O$ or O or $OR^5O$
or $R^1=H$;
$R^2=H$ or $CH_3$ or
$R^2=CH_2COOR^3$ and $Q\neq CH_2O$ or O or $OR^5O$ or
$R^2=CH_2QA_mB_nA_pR$ and $Q\neq CH_2O$ or O or $OR^5O$;
$R^3=H$ or $C_1-C_8$ alkyl;
$Q=O$ or $OR^5O$ provided that $R^1$ and $R^2=H$ or
$Q=CH_2O$, COO or $CONR^4$ where $R^4=H$ or $CH_3$ and $R^5=C_{1-4}$ alkylene The hydrophobic group can therefore be introduced as, for instance, an acrylic ester of a surfactant alcohol or other group described in the patents listed above, but preferably the hydrophobic group is introduced as an allyl ether of a surfactant alcohol. Thus the monomer preferably has the formula $CH_2=CR'CH_2OA_mB_nA_pR$ where R' is hydrogen or methyl.

The allyl ethers may be made by methods such as those described in GB No. 1,273,552, for instance by reacting an appropriate surfactant alcohol with sodium or sodium alkoxide, generally in the absence of water but in a solvent such as xylene, to form the sodium derivative and then reacting this with allyl chloride, or by reacting allyl alcohol with the surfactant alcohol with or without catalyst. Preferably however the allyl ethers are made by the method described in our copending application inventors Farrar and Hawe, filed even date herewith in published Monomer Production European patent application EP-A-No. 213800.

Water insoluble monomer (b) may be present, for instance to control the degree of swelling of the polymer, in amounts up to 40% but the amount is generally below 20% and it is generally best for the polymer to be free of water insoluble monomer. By water insoluble monomer in this specification we mean a monomer soluble in water to the extent of less than 5% at room temperature. If such monomer is to be incorporated then it may be, for instance, styrene, acrylonitrile, vinyl chloride or vinyl acetate but is preferably an alkyl, hydroxy alkyl or alkoxy alkyl (meth) acrylate most preferably a $C_{1-4}$ alkyl (meth) acrylate.

The water soluble monomer (a) can be a single monomer or a monomer blend and the monomers may be cationic, non-ionic or anionic and are usually vinyl monomers, especially acrylic monomers.

Suitable cationic monomers are cationic tertiary amines for instance dialkylaminoalkyl (meth) acrylates (generally as acid or quaternary ammonium salts). Any alkyl groups generally contain up to four carbon atoms and the preferred monomers are dialkylaminoethyl (meth) acrylates, especially when alkyl=methyl. Other suitable cationic monomers that may be used include dialkylaminoalkyl (meth) acrylamides where the aminoalkyl group generally includes an alkylene group of 2 to 8 carbon atoms, preferably 1,3-propylene, e.g., dimethylamino-1,3-propylene methacrylamide. Cationic monomers are usually used blended with 20 to 95%, generally 60 to 95%, non-ionic monomer by weight of the blend of water soluble monomers).

The preferred anionic monomers are ethylenically unsaturated carboxylic and sulphonic acids, generally as water soluble salts such as the sodium salt. Suitable acids are allyl sulphonic acid, 2-acrylamido-2-methyl propane sulphonic acid, methacrylic acid, itaconic acid, crotonic acid or, preferably, acrylic acid. In some polymers the water soluble monomer consists only of anionic monomer, for instance sodium acrylate, but in many polymers the anionic monomer is blended with a non-ionic monomer, the amount of non-ionic monomer in the blend generally being from 2 to 80%, often 30 to 70% by weight of the blend.

Non-ionic monomer can be used by itself, but generally in combination with cationic or anionic monomer. The preferred non-ionic monomer is acrylamide.

One preferred group of polymers are terpolymers of 3 to 30% of the allyl ether or other monomer carrying the hydrophobe, 20 to 60% sodium acrylate and 30 to 70% acrylamide.

Another preferred group of polymers are formed from 3 to 30% of the allyl ether or other group carrying the hydrophobe and 97 to 70% of sodium acrylate and 0 to 20% acrylamide.

Another preferred group of polymers are terpolymers of 3 to 30% monomer (d), usually an allyl ether, 20 to 60% dialkylaminoalkyl (meth) -acrylate or dialkylaminoalkyl (meth) -acrylamide or acid salt or quaternised derivatives where the alkyl groups contain up to 4 carbon atoms with 30–70% acrylamide. Polymers containing cationic groups are particularly useful where the fluid to be absorbed contains multivalent metal ions.

Any of the cross linking agents typically used for cross linking water swellable polymers may be used. A typical polyethylenically unsaturated monomer is methylene bis acrylamide. Ionic cross linking agents can be used, e.g., aluminium sulphate. The amount of cross linking agent is generally below 1% and preferably is from 0.0005 to 0.5% (5 to 5,000 ppm), most preferably 0.01 to 0.2%. The amount of cross linking agent is preferably such that the polymer has an absorptive capacity for deionised water of from 50 to 1000 ml per gram dry polymer, and an absorptive capacity for the aqueous phase that it is to absorb of at least 30 and preferably at least 100.

The polymer may be made by gel polymerisation followed by drying and comminution in conventional manner or as described in EP No. 0169674. Alternatively the polymer may be made by reverse phase bead polymerisation, followed by azeotropic distillation and filtration in conventional manner. The dry particle size is generally from 50 to 2000 μm, preferably 100 to 1000 μm, e.g., 200 to 700 μm. The dry particle size is the size of the particles when substantially dry, i.e., when dried to ambient atmospheric moisture content.

The polymerisation conditions are preferably such that if the polymer was made under the identical conditions but free of cross linker it would have IV (single point intrinsic viscosity measured in sodium chloride at 25° C. at 0.05% polymer concentration) of at least 1, generally at least 2 and usually at least 3, for instance 5 to 10 or even higher, for instance up to 20 or more such as are typically obtainable from the monomers (a) and (b) in the absence of (c) and (d).

It is preferred in the invention to use one of the allyl ether monomers described above and it is very surprising that these high molecular weight allyl ether polymers can be made because such molecular weights clearly were not obtained in the processes of GB Nos. 1,167,524 and 1,273,552, conventional beliefs relating to polymerisation of allyl monomers indicate that low molecular weights would be obtained, and these high molecular weights have only rarely been obtained even with polymers in which the hydrophobic group is connected by an acrylic ester linkage. The reason for our being able to obtain the high molecular weights is not clear but may be due to the effect of the group $-A_mB-_nA_pR$ on the polymerisation properties of the monomer.

The surface of the particles is preferably less swellable than the inner parts of the particles, preferably as a result of cross linking the surface layer. This treatment can reduce the stickiness of the particles and can improve the absorption properties, especially when the polymer contains at least 70% of an anionic monomer.

It is already known to minimise aggregation of swellable polymer particles upon addition to water by providing the particles with a surface layer of reduced swellability, generally by cross linking, and any of these known methods may be used in the invention. The cross linking can be achieved by contacting the surfaces of the particles with a polyvalent metal salt or other cross linking agent. For instance in U.S. Pat. Nos. 3,114,651 and 3,251,814 particles are treated with a chromic salt. In JP No. 1983/42602 an insoluble water absorbent cross linked polymer is dispersed in a medium containing polyvalent metal salt or epihalohydrin. Other methods and materials are described in U.S. Pat. Nos. 4,043,952 and 4,090,013. Another method comprises coating anionic particles with a cationic polymer, such as a polymer of diallyl dimethyl ammonium chloride, e.g., during comminution of the polymer. In another method we apply to the particles a solution in a solvent or solvent blend of sodium aluminate or other aluminate.

The absorbent polymers can be used in any environment where an aqueous medium is to be absorbed, e.g., wherever cross linked swellable particles of sodium polyacrylate (optionally copolymerised with acrylamide) have been used previously. They are of particular value when the medium contains an electrolyte. The presence of the pendant hydrophobic group greatly improves the absorptive capacity of aqueous electrolytes compared to the corresponding polymers free of such groups.

The polymers are generally used in a situation that they absorb all the free fluid and so are not surrounded by a continuous aqueous phase but are instead surrounded by, for instance, air.

The invention includes processes in which the polymer particles are used as absorbents as well as compositions and other products in which they are acting as absorbents. The polymers are of particular value as absorbents in diapers and may be incorporated in them in conventional manner and in conventional amounts. The particles can also be used as absorbents in other personal hygiene absorbent products, such as bandages. They can be used for dewatering slurries or for the other purposes described in EP No. 86301521.0. They can be used for conditioning soil or for promoting growth characteristics of soil or other culture medium, for instance as described in EP No. 0101253. They can be used as a diverter for preflush and acidising applications downhole.

The amount of polymer will be selected having regard to the absorptive capacity of the polymer for the particular aqueous medium that is to be absorbed. Generally the polymer will be present in an amount 0 to 100% above the amount required for absorption of all the aqueous medium.

EXAMPLE 1

A range of polymers were made by gel polymerisation using differing amounts of acrylamide, sodium acrylate, allyl ether and cross linking agent, and by using different monomers (d) which are all allyl ethers. The product of the polymerisation was then dried and comminuted to give particles having sizes in the range 200 to 500 microns.

0.5 g of each polymer was added to 400 cc of a swelling solution that was deionised water or aqueous sodium chloride of various concentrations. The samples were allowed to equilibrate for 30 minutes and the swollen gel particles were then separated from the medium by filtration through a nylon filter mesh and weighed to give an indication of absorbency. The values are expressed in percentage based on the amount of deionised water that was absorbed by each polymer. The monomer feed and the results are shown in the following table. In this table R is the hydrophobic group and n is the number of ethylene oxide groups between it and the allyl ether linkage.

| Polymer | 1 | 2 | 3 | 4 | 5 | 6 | 7 | 8 |
|---|---|---|---|---|---|---|---|---|
| Acrylamide | 60 | 50 | 45 | 45 | 50 | 50 | 50 | 50 |
| Sodium Acrylate | 40 | 40 | 40 | 40 | 40 | 40 | 40 | 40 |
| Methylene bis acrylamide | 0.03 | 0.06 | 0.06 | 0.06 | 0.03 | 0.06 | 0.03 | 0.06 |
| Allyl ether | 0 | 10 | 15 | 15 | 10 | 10 | 10 | 10 |
| R | — | $C_{18}H_{37}$ | $C_{18}H_{37}$ | $C_{18}H_{37}$ | $C_{12}H_{25}$ | $C_{12}H_{25}$ | $C_{18}H_{37}$ | $C_{18}H_{37}$ |
| n | — | 10 | 10 | 20 | 23 | 23 | 20 | 20 |
| Deionized water | 100 | 100 | 100 | 100 | 100 | 100 | 100 | 100 |
| 0.1% NaCl | 21.7 | 32.4 | 25.5 | 33.8 | 27.3 | 21.8 | 25.1 | 34.0 |
| 0.25% NaCl | 12.5 | 22.4 | 16.7 | 22.9 | 18.8 | 14.9 | 16.6 | 23.8 |
| 0.5% NaCl | 10.3 | 16.5 | 11.6 | 14.9 | 15.1 | 11.6 | 11.9 | 17.4 |
| 1% NaCl | 7.9 | 8.8 | 10.0 | 11.2 | 11.6 | 7.9 | 9.8 | 13.6 |

Comparison of polymers 3 and 4 shows the advantage that follows from increasing the length of the ethoxy clain. Very poor results are obtained when there is no ethoxy chain, as in U.S. Pat. No. 4,190,562.

EXAMPLE 2

Example 1 can be repeated except that the allyl ether is omitted and is replaced by either a diester formed between itaconic acid and the corresponding ethoxylate of stearyl alcohol or by the monoester formed between arcylic acid and the ethoxylate of stearyl alcohol.

EXAMPLE 3

The process of example 1 can be repeated except that the particles can be sprayed with aqueous aluminium sulphate solution and then allowed to dry, before being used as absorbents.

We claim:

1. An absorbent polymer comprising water insoluble, water-swellable particles having a dry size of at least 20 μm and formed from monomers comprising (a) 30 to 99% by weight water soluble ethylenically unsaturated monomer, said water soluble ethylenically unsaturated monomer selected from dialkylaminoalkyl (meth) acrylates, dialkylaminoalkyl (meth) acrylamides and their acid salts and quaternized derivatives, ethylenically unsaturated carboxylic and sulphonic acids, and non-ionic monomers, (b) 0 to 40% water insoluble ehtylenically unsaturated monomer, and (c) 0.0001 to 1% by weight cross linking agent, and characterized in that the monomers include 3 to 50% by weight of a monomer having the formula $R^1CH=C(R^2)QB_nR$ where Q is selected from $CH_2O$ or COO, $R^1$ is hydrogen or COOH, $R^2$ is hydrogen or methyl, and wherein B is ethyleneoxy, n is at least 5, and R is a hydrophobic group which is a hydrocarbyl group of 8 to 30 carbon atoms selected from alkyl, aralkyl, aryl, alkaryl and cycloalkyl such that the polymer has an absorptive capacity of at least 50 ml deionised water per gram of dry polymer and wherein the absorptive capacity of the polymer for 0.25% aqueous NaCl is greater when R is the said hydrophobic group than when R is methyl or hydrogen.

2. A polymer according to claim 1 in which R is a hydrocarbyl group containing 10 to 24 carbon atoms and selected from alkyl and alkaryl.

3. A polymer according to claim 1 in which the monomer has the formula $CH_2=CR_2'CH_2OB_nR$ where $R_2'$ is selected from hydrogen and methyl.

4. A polymer according to claim 1 in which monomer (a) comprises 20 to 100% ionic monomer with 0 to 80% non-ionic monomer, the amounts being by weight of monomer (a).

5. A polymer according to claim 1 in which monomer (a) comprises 20 to 100% of a monomer selected from dialkylaminoalkyl (meth) -acrylates and -acrylamides and their acid salt and quaternised derivatives, where the alkyl groups contain up to 4 carbon atoms, and sodium acrylate with 0 to 80% acrylamide.

6. A polymer according to claim 1 comprising 3 to 30% by weight of monomer, selected from 20 to 60% by weight of dialkylaminoalkyl (meth) -acrylates and -acrylamides and their acid salt and quaternised derivatives, in which the alkyl groups contain up to 4 carbon atoms, with sodium acrylate and 30 to 70% by weight acrylamide, and (c) 0.0005 to 0.1% cross linking agent.

7. A polymer according to claim 1 formed from 3 to 30% by weight of monomer (a) selected from 97 to 70% by weight of dialkylaminoalkyl (meth) -acrylates and -acrylamides, and (c) their acid salt and quaternised derivatives, where the alkyl groups contain up to 4 carbon atoms, and sodium acrylate with 0 to 20% by weight acrylamide and 0.0005 to 0.1% cross linking agent.

8. A diaper containing absorbent polymer according to claim 1.

9. A polymer according to claim 1 in which n is 10 to 100.

10. An absorbent polymer comprising water insoluble, water-swellable particles have a dry size of at least 20 μm and formed from monomers comprising (a) 30 to 99% by weight water soluble ethylenically unsaturated monomer, said water soluble ethylenically unsaturated monomer comprises 20 to 100% of a monomer selected from dialkylaminoalkyl (meth) -acrylates and -acrylamides and their acid salts and quaternised derivatives, where the alkyl groups contain up to 4 carbon atoms, ans sodium acrylate with 0 to 80% acylamide, (b) 0 to 40% water insoluble ethylenically unsaturated monomer, and (c) 0.0001 to 1% by weight cross linking agent, and characterised in that the monomers include 3 to 50% by weight of a monomer having the formula $R^1CH=C(R^2)QB_nR$ where Q is selected from $CH_2O$ or COO, $R^1$ is hydrogen or COOH, $R^2$ is hydrogen or methyl, and wherein B is ethyleneoxy, n is at least 5 and R is a hydrophobic group which is a hydrocarbyl group of 8 to 30 carbon atoms selected from alkyl, aralkyl, aryl, alkaryl and cycloalkyl and wherein the absorptive capacity of the polymer for 0.25% aqueous NaCl is greater when R is the said hydrophobic group than when R is methyl or hydrogen.

11. A polymer according to claim 10 in which the monomer has the formula $CH_2=CR_2'CH_2OB_nR$ where R' is selected from hydrogen and methyl.

12. An absorbent polymer comprising water insoluble, water-swellable particles having a dry size of at least 20 μm and formed from monomers comprising (a) 30 to 99% by weight water soluble ethylenically unsaturated monomer, said water soluble ethylenically unsaturated monomer selected from dialkylaminoalkyl (meth) -acrylates, dialkylaminoalkyl (meth) acrylamides and their acid salts and quaternized derivatives, ethylenically unsaturated carboxylic and sulphonic acids, and non-ionic monomers, (b) 0 to 40% water insoluble ethylenically unsaturated monomer, and (c) 0.0001 to 1% by weight cross linking agent, and characterized in that the monomers include 3 to 50% by weight of a monomer having the formula $R^1CH=C(R^2)QB_nR$ where Q is selected from $CH_2O$ or COO, $R^1$ is hydrogen or COOH, $R^2$ is hydrogen or methyl, and wherein B is ethyleneoxy, n is at least 5, and R is a hydrophobic group which is a hydrocarbyl group of 12 to 18 carbon atoms and wherein the absorptive capacity of the polymer for 0.25% aqueous NaCl is methyl or hydrogen.

13. An absorbent polymer comprising water insoluble, water-swellable particles having a dry size of at least 20 μm and formed from monomers comprising (a) 30 to 99% by weight water soluble ethylenically unsaturated monomer, said water soluble ethylenically unsaturated monomer comprises 20 to 100% of a monomer selected from dialkylaminoalkyl (meth) -acrylates and -acrylamides and their acid salts and quaternised derivatives, where the alkyl groups contain up to 4 carbon atoms, and sodium acrylate with 0 to 80% acrylamide (b) 0 to 40% water insoluble ethylenically unsaturated monomer, and (c) 0.0001 to 1% by weight cross linking agent, and characterised in that the monomers include 3 to 50% by weight of a monomer having the formula $R^1CH=C(R^2)QB_nR$ where Q is selected from $CH_2O$ or COO, $R^1$ is hydrogen or COOH, $R^2$ is hydrogen or methyl, and wherein B is ethyleneoxy, n is at least 5, and R is a hydrophobic group which is a hydrocarbyl group of 12 to 18 carbon atoms and wherein the absorptive capacity of the polymer for 0.25% aqueous NaCl is greater when R is the said hydrophobic group than when R is methyl or hydrogen.

* * * * *

UNITED STATES PATENT AND TRADEMARK OFFICE
CERTIFICATE OF CORRECTION

PATENT NO. : 4,980,434
DATED : December 25, 1990
INVENTOR(S) : DAVID FARRAR ET AL It is certified that error appears in the above-identified patent and that said Letters Patent is hereby corrected as shown below:

Claim 1, Col. 7, Lines 28-29, Delete "ehtylenically" and substitute therefore --- ethylenically ---; Claim 10, Col. 8, Line 20, delete "ans" and substitute therefore --- and ---; Claim 11, Col. 8, Line 36, delete "$CH_2=CR_2'CH_2OB_nR$ and substitute therefore ---$CH_2=CR_2CH_2OB_NR$-- ---; Claim 12, Col. 8, Line 56, after "NaCl", insert --- is greater when R is the said hydrophobic group than when R ---.

Signed and Sealed this

Fourth Day of August, 1992

*Attest:*

DOUGLAS B. COMER

*Attesting Officer*   Acting Commissioner of Patents and Trademarks